US012616790B2

(12) United States Patent
Barrett et al.

(10) Patent No.: US 12,616,790 B2
(45) Date of Patent: May 5, 2026

(54) PUMPING MECHANISM WITH WIRE-PULLED PLUNGER

(71) Applicant: Insulet Corporation, Acton, MA (US)

(72) Inventors: Daniel Barrett, Somerville, MA (US);
Soroush Kamrava, Everett, MA (US);
Maureen Mccaffrey, Arlington, MA
(US)

(73) Assignee: INSULET CORPORATION, Acton,
MA (US)

( * ) Notice: Subject to any disclaimer, the term of this
patent is extended or adjusted under 35
U.S.C. 154(b) by 511 days.

(21) Appl. No.: 17/674,113

(22) Filed: Feb. 17, 2022

(65) Prior Publication Data

US 2022/0288302 A1     Sep. 15, 2022

Related U.S. Application Data

(60) Provisional application No. 63/306,765, filed on Feb.
4, 2022, provisional application No. 63/160,240, filed
on Mar. 12, 2021.

(51) Int. Cl.
*A61M 5/142*      (2006.01)
*A61M 5/145*      (2006.01)
*A61M 5/315*      (2006.01)

(52) U.S. Cl.
CPC .... *A61M 5/14232* (2013.01); *A61M 5/14248*
(2013.01); *A61M 5/1452* (2013.01);
(Continued)

(58) Field of Classification Search
CPC ........... A61M 2005/31518; A61M 2005/3152;
A61M 5/14248; A61M 5/1452;
(Continued)

(56) References Cited

U.S. PATENT DOCUMENTS 1,441,508 A     1/1923   Jensen
2,198,666 A     4/1940   Gruskin
(Continued)

FOREIGN PATENT DOCUMENTS

CA          606281 A     10/1960
CN         1375338 A     10/2002
(Continued)

OTHER PUBLICATIONS

International Search Report and Written Opinion for PCT Applica-
tion No. PCT/US2019/059854, mailed Aug. 26, 2020, 15 pages.
(Continued)

*Primary Examiner* — Emily L Schmidt
*Assistant Examiner* — Samuel J Marrison
(74) *Attorney, Agent, or Firm* — Goodwin Procter LLP

(57)          ABSTRACT
Disclosed herein are devices and methods for causing the
linear translation of a plunger through a reservoir containing
a fluid. A flexible member, for example, a wire or a ribbon,
is coupled to the plunger and extends through a wall of the
reservoir toward which the plunger is being linearly trans-
lated. A pulling force on the flexible member caused by a
drive mechanism causes the plunger to linearly translate
toward the end wall of the reservoir, thereby forcing any
fluid contained in the reservoir out of the reservoir through
a fluid port.

23 Claims, 7 Drawing Sheets

(52) U.S. Cl.
 CPC ............. *A61M 2005/14252* (2013.01); *A61M 2005/1426* (2013.01); *A61M 2005/31518* (2013.01); *A61M 2205/0266* (2013.01); *A61M 2205/3592* (2013.01)

(58) Field of Classification Search
 CPC ...... A61M 2005/14533; A61M 60/279; A61M 60/284; A61M 25/0113; F04B 17/00; F04B 17/03
 USPC ......................................................... 417/362
 See application file for complete search history.

(56) References Cited

U.S. PATENT DOCUMENTS

| | | | |
|---|---|---|---|
| 2,752,918 A | 7/1956 | Uytenbogaar | |
| 3,176,712 A | 4/1965 | Ramsden | |
| 3,297,260 A | 1/1967 | Barlow | |
| 3,464,359 A | 9/1969 | King | |
| 3,786,811 A * | 1/1974 | Holbrook ............ | A61M 5/3129 604/218 |
| 3,885,662 A | 5/1975 | Schaefer | |
| 3,946,732 A | 3/1976 | Hurscham | |
| 3,947,692 A | 3/1976 | Payne | |
| 3,993,061 A | 11/1976 | OLeary | |
| 4,108,177 A | 8/1978 | Pistor | |
| 4,152,098 A | 5/1979 | Moody et al. | |
| 4,210,173 A | 7/1980 | Choksi et al. | |
| 4,221,219 A | 9/1980 | Tucker | |
| 4,257,324 A | 3/1981 | Stefansson et al. | |
| 4,268,150 A | 5/1981 | Chen | |
| 4,277,226 A | 7/1981 | Archibald | |
| 4,313,439 A | 2/1982 | Babb et al. | |
| 4,371,790 A | 2/1983 | Manning et al. | |
| 4,417,889 A | 11/1983 | Choi | |
| 4,424,720 A | 1/1984 | Bucchianeri | |
| 4,435,173 A | 3/1984 | Siposs et al. | |
| 4,475,905 A | 10/1984 | Himmelstrup | |
| 4,498,843 A | 2/1985 | Schneider et al. | |
| 4,507,115 A | 3/1985 | Kambara et al. | |
| 4,551,134 A | 11/1985 | Slavik et al. | |
| 4,562,751 A | 1/1986 | Nason et al. | |
| 4,567,549 A | 1/1986 | Lemme | |
| 4,585,439 A | 4/1986 | Michel | |
| 4,601,707 A | 7/1986 | Albisser et al. | |
| 4,634,427 A | 1/1987 | Hannula et al. | |
| 4,671,429 A | 6/1987 | Spaanderman et al. | |
| 4,678,408 A | 7/1987 | Nason et al. | |
| 4,684,368 A | 8/1987 | Kenyon | |
| 4,685,903 A | 8/1987 | Cable et al. | |
| 4,755,169 A | 7/1988 | Sarnoff et al. | |
| 4,766,889 A | 8/1988 | Trick et al. | |
| 4,808,161 A | 2/1989 | Kamen | |
| 4,846,797 A | 7/1989 | Howson et al. | |
| 4,858,619 A | 8/1989 | Toth | |
| 4,898,579 A | 2/1990 | Groshong et al. | |
| 4,908,017 A | 3/1990 | Howson et al. | |
| 4,944,659 A | 7/1990 | Labbe et al. | |
| 4,969,874 A | 11/1990 | Michel et al. | |
| 4,991,743 A | 2/1991 | Walker | |
| 5,007,458 A | 4/1991 | Marcus et al. | |
| 5,020,325 A | 6/1991 | Henault | |
| 5,062,841 A | 11/1991 | Siegel | |
| 5,147,311 A | 9/1992 | Pickhard | |
| 5,178,609 A | 1/1993 | Ishikawa | |
| 5,205,819 A | 4/1993 | Ross et al. | |
| 5,213,483 A | 5/1993 | Flaherty et al. | |
| 5,222,362 A | 6/1993 | Maus et al. | |
| 5,236,416 A | 8/1993 | McDaniel et al. | |
| 5,261,882 A | 11/1993 | Sealfon | |
| 5,261,884 A | 11/1993 | Stern et al. | |
| 5,277,338 A | 1/1994 | Divall et al. | |
| 5,281,202 A | 1/1994 | Weber et al. | |
| 5,346,476 A | 9/1994 | Elson | |
| 5,364,342 A | 11/1994 | Beuchat et al. | |
| 5,388,615 A | 2/1995 | Edlund et al. | |

| | | | |
|---|---|---|---|
| 5,433,710 A | 7/1995 | VanAntwerp et al. | |
| 5,503,628 A | 4/1996 | Fetters et al. | |
| 5,520,661 A | 5/1996 | Lal et al. | |
| 5,533,389 A | 7/1996 | Kamen et al. | |
| 5,582,593 A | 12/1996 | Hultman | |
| 5,618,269 A | 4/1997 | Jacobsen et al. | |
| 5,628,309 A | 5/1997 | Brown | |
| 5,637,095 A * | 6/1997 | Nason ............... | A61M 5/14244 604/154 |
| 5,665,070 A | 9/1997 | McPhee | |
| 5,713,875 A | 2/1998 | Tanner, II | |
| 5,747,350 A | 5/1998 | Sattler | |
| 5,748,827 A | 5/1998 | Holl et al. | |
| 5,776,103 A | 7/1998 | Kriesel et al. | |
| 5,779,676 A | 7/1998 | Kriesel et al. | |
| 5,785,688 A | 7/1998 | Joshi et al. | |
| 5,797,881 A | 8/1998 | Gadot | |
| 5,800,397 A | 9/1998 | Wilson et al. | |
| 5,807,075 A | 9/1998 | Jacobsen et al. | |
| 5,839,467 A | 11/1998 | Saaski et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,957,890 A | 9/1999 | Mann et al. | |
| 5,961,492 A | 10/1999 | Kriesel et al. | |
| 5,971,963 A | 10/1999 | Choi | |
| 6,019,747 A | 2/2000 | McPhee | |
| 6,050,457 A | 4/2000 | Arnold et al. | |
| 6,068,615 A | 5/2000 | Brown et al. | |
| 6,159,188 A | 12/2000 | Laibovitz et al. | |
| 6,174,300 B1 | 1/2001 | Kriesel et al. | |
| 6,190,359 B1 | 2/2001 | Heruth | |
| 6,200,293 B1 | 3/2001 | Kriesel et al. | |
| 6,352,522 B1 | 3/2002 | Kim et al. | |
| 6,363,609 B1 | 4/2002 | Pickren | |
| 6,375,638 B2 | 4/2002 | Nason et al. | |
| 6,474,219 B2 | 11/2002 | Klitmose et al. | |
| 6,485,461 B1 | 11/2002 | Mason et al. | |
| 6,485,462 B1 | 11/2002 | Kriesel | |
| 6,488,652 B1 | 12/2002 | Weijand et al. | |
| 6,520,936 B1 | 2/2003 | Mann | |
| 6,527,744 B1 | 3/2003 | Kriesel et al. | |
| 6,537,249 B2 | 3/2003 | Kriesell et al. | |
| 6,539,286 B1 | 3/2003 | Jiang | |
| 6,569,115 B1 | 5/2003 | Barker et al. | |
| 6,595,956 B1 | 7/2003 | Gross et al. | |
| 6,656,158 B2 | 12/2003 | Mahoney et al. | |
| 6,699,218 B2 | 3/2004 | Flaherty et al. | |
| 6,723,072 B2 | 4/2004 | Flaherty et al. | |
| 6,740,059 B2 | 5/2004 | Flaherty | |
| 6,749,407 B2 | 6/2004 | Xie et al. | |
| 6,851,260 B2 | 2/2005 | Mernoe | |
| 6,883,778 B1 | 4/2005 | Newton et al. | |
| 7,018,360 B2 | 3/2006 | Flaherty et al. | |
| 7,104,275 B2 | 9/2006 | Dille | |
| 7,128,727 B2 | 10/2006 | Flaherty et al. | |
| 7,137,964 B2 | 11/2006 | Flaherty | |
| 7,160,272 B1 | 1/2007 | Eyal et al. | |
| 7,303,549 B2 | 12/2007 | Flaherty | |
| 7,771,392 B2 | 8/2010 | De Polo et al. | |
| 7,914,499 B2 | 3/2011 | Gonnelli et al. | |
| 7,951,114 B2 | 5/2011 | Rush et al. | |
| 8,267,921 B2 | 9/2012 | Yodfat et al. | |
| 8,382,703 B1 | 2/2013 | Abdelaal | |
| 8,499,913 B2 | 8/2013 | Gunter | |
| 8,905,995 B2 | 12/2014 | Mernoe | |
| 8,920,376 B2 | 12/2014 | Caffey et al. | |
| 8,939,935 B2 | 1/2015 | OConnor et al. | |
| 9,180,244 B2 | 11/2015 | Anderson et al. | |
| 9,192,716 B2 | 11/2015 | Jugl et al. | |
| 9,402,950 B2 | 8/2016 | Dilanni et al. | |
| 9,539,596 B2 | 1/2017 | Ikushima | |
| 10,441,723 B2 | 10/2019 | Nazzaro | |
| 10,695,485 B2 | 6/2020 | Nazzaro | |
| 2001/0016710 A1 | 8/2001 | Nason et al. | |
| 2001/0056258 A1 | 12/2001 | Evans | |

(56)            References Cited

U.S. PATENT DOCUMENTS

| | | |
|---|---|---|
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | DAntonio et al. |
| 2003/0055380 A1 | 3/2003 | Flaherty |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0073228 A1* | 3/2007 | Mernoe ............ A61M 5/14566 |
| | | 604/131 |
| 2007/0073236 A1 | 3/2007 | Merno et al. |
| 2007/0088271 A1 | 4/2007 | Richards |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0243211 A1 | 10/2008 | Cartwright et al. |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0073620 A1 | 3/2011 | Verrilli |
| 2011/0144586 A1 | 6/2011 | Michaud et al. |
| 2011/0180480 A1 | 7/2011 | Kloeffel et al. |
| 2011/0230833 A1 | 9/2011 | Landman et al. |
| 2012/0078161 A1 | 3/2012 | Masterson et al. |
| 2012/0172804 A1 | 7/2012 | Plumptre |
| 2012/0172817 A1 | 7/2012 | Bruggemann et al. |
| 2012/0209207 A1 | 8/2012 | Gray et al. |
| 2013/0006213 A1 | 1/2013 | Arnitz et al. |
| 2013/0017099 A1 | 1/2013 | Genoud |
| 2013/0064701 A1 | 3/2013 | Konishi |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0274657 A1* | 10/2013 | Zirps ................ A61M 25/0147 |
| | | 604/95.01 |
| 2013/0296792 A1 | 11/2013 | Cabiri |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2014/0277420 A1* | 9/2014 | Migliazza ............. A61F 2/2448 |
| | | 29/428 |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0209505 A1* | 7/2015 | Hanson ............. A61M 5/14566 |
| | | 604/135 |
| 2015/0246176 A1* | 9/2015 | Navarro ................ A61M 5/172 |
| | | 604/151 |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamer |
| 2016/0055842 A1 | 2/2016 | Defranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213837 A1* | 7/2016 | Schabbach ........ A61M 5/14244 |
| 2016/0213851 A1 | 7/2016 | Weibel et al. |
| 2016/0278899 A1 | 9/2016 | Heller et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0345931 A1 | 11/2020 | Gray et al. |
| 2021/0236771 A1* | 8/2021 | Turner ............. A61M 25/0113 |

FOREIGN PATENT DOCUMENTS

| | | |
|---|---|---|
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| EP | 3508236 A1 | 7/2019 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | H06296690 A | 10/1994 |

(56)                    References Cited

FOREIGN PATENT DOCUMENTS

| JP | H08238324 | A  | 9/1996 |
| JP | 2004247271 | A  | 9/2004 |
| JP | 2004274719 | A  | 9/2004 |
| JP | 2005188355 | A  | 7/2005 |
| JP | 2006159228 | A  | 6/2006 |
| JP | 6098988 | B2 | 9/2006 |
| JP | 2006249130 | A  | 9/2006 |
| JP | 2009514580 | A  | 4/2009 |
| JP | 2017513577 | A  | 6/2017 |
| NL | 1019126 | C1 | 4/2003 |
| WO | 8101658 | A1 | 6/1981 |
| WO | 8606796 | A1 | 11/1986 |
| WO | 9320864 | A1 | 10/1993 |
| WO | 9415660 | A1 | 7/1994 |
| WO | 9855073 | A1 | 12/1998 |
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009141005 | A1 | 11/2009 |
| WO | 2010022069 | A2 | 2/2010 |
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014179774 | A1 | 11/2014 |
| WO | 2015032772 | A1 | 3/2015 |
| WO | 2015048791 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017148855 | A1 | 9/2017 |
| WO | 2017187177 | A1 | 11/2017 |
| WO | 2021016452 | A1 | 1/2021 |

OTHER PUBLICATIONS

International Search Report and Written Opinion, Application No. PCT/US2022/016713, mailed Aug. 5, 2022, 19 pages.
European Search Report and Written Opinion for European Patent Application No. EP20174878, dated Sep. 29, 2020, 4 pages.
Schott web-page image from Jul. 9, 2016, https://www.us.schott.com/pharmaceutical_packaging/english/products/cartridges.html.
International Search Report and Written Opinion for International Patent Application No. PCT/US2021/055581, dated Feb. 8, 2022, 19 pages.
International Search Report and Written Opinion for International Patent Application No. PCT/US2022/011356, dated Apr. 29, 2022, 19 pages.
International Search Report and Written Opinion for International Patent Application No. PCT/US2022/029012, mailed Aug. 19, 2022, 12 pages.
International Search Report and Written Opinion for PCT/US2018/014351, mailed on Jun. 4, 2018, 9 pages.
Lind et al. "Linear Motion Miniature Actuators." Paper presented at the 2nd Tampere International Conference on Machine Automation, Tampere, Finland (Sep. 1998).
Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.
Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.
Vaughan, M.E., "The Design, Fabrication, and Modeling of a Piezoelectric Linear Motor." Master's thesis, Virginia Polytechnic Institute and State University, VA. (2001).
Galante et al., "Design, Modeling, and Performance of a High Force Piezoelectric Inchworm Motor," Journal of Intelligent Material Systems and Structures, vol. 10, 962-972 (1999).
International Search Report and Written Opinion for International Application No. PCT/US2017/055054, mailed on Jan. 25, 2018, 13 pages.
International Search Report and Written Opinion for International Application No. PCT/US2018/045155, mailed on Oct. 15, 2018, 15 pages.
International Preliminary Report on Patentability for International Application No. PCT/US2017/034811 issued on Nov. 27, 2018, 10 pages.
International Preliminary Report on Patentability for International Patent Application No. PCT/US2017/046508, Feb. 12, 2019, 10 pages.
International Search Report and Written Opinion for International Application No. PCT/US2017/046508, mailed on Jan. 17, 2018, 14 pages.
International Search Report and Written Opinion for International Application No. PCT/US2017/046777, mailed on Dec. 13, 2017, 14 pages.
International Search Report and Written Opinion for International Application No. PCT/US2017/046737, mailed on Dec. 14, 2017, 11 pages.
International Search Report and Written Opinion for International Application No. PCT/US2017/034814, mailed on Oct. 11, 2017, 18 pages.
European Search Report and Written Opinion for the European Patent Application No. EP19177571, dated Oct. 30, 2019, 8 pages.
International Preliminary Report on Patentability for International Patent Application No. PCT/US2018/014351, dated Jul. 23, 2019, 7 pages.
International Preliminary Report on Patentability for International Patent Application No. PCT/US2017/046777, dated Feb. 19, 2019, 8 pages.
International Preliminary Report on Patentability for International Patent Application No. PCT/US2017/046737, dated Feb. 19, 2019, 8 pages.
International Preliminary Report on Patentability for International Patent Application No. PCT/US2017/055054, dated Apr. 9, 2019, 8 pages.
International Search Report and Written Opinion for Application No. PCT/US2017/034811, mailed Oct. 18, 2017, 15 pages.
EPO Search Report received in Application No. 13768938.6, dated Nov. 11, 2015, 8 pages.
International Search Report and Written Opinion for PCT Application No. PCT/US13/34674, mailed Aug. 6, 2013, 17 pages.
International Search Report and Written Opinion for International Application No. PCT/GB2007/004073, Jan. 31, 2008, 8 pages.
International Search Report and Written Opinion for International Patent Application No. PCT/US2019/063615, dated May 3, 2020, 17 pages.

(56)                   References Cited

OTHER PUBLICATIONS

International Preliminary Report on Patentability for International Patent Application No. PCT/US2018/045155, dated Feb. 14, 2020, 10 pages.
International Search Report and Written Opinion for International Patent Application No. PCT/US2019/035756, dated Jul. 31, 2019, 11 pages.

* cited by examiner

PUMPING MECHANISM WITH WIRE-PULLED PLUNGER

RELATED APPLICATIONS

This application claims the benefit of U.S. Provisional Patent Application No. 63/160,240, filed Mar. 12, 2021, entitled "IMPROVED DRIVE MECHANISMS FOR POSITIVE DISPLACEMENT PUMPS", and U.S. Provisional Patent Application No. 63/306,765, filed Feb. 4, 2022, entitled "PUMPING MECHANISM WITH WIRE-PULLED PLUNGER". The contents of these application are incorporated herein in their entireties.

BACKGROUND

Many conventional automatic drug delivery systems are well known, including, for example, wearable drug delivery devices of the type shown in FIG. 2. The drug delivery device 102 can be designed to deliver any type of liquid drug to a user. In specific embodiments, the drug delivery device 102 can be, for example, an OmniPod® drug delivery device manufactured by Insulet Corporation of Acton, Massachusetts. The drug delivery device 102 can be a drug delivery device such as those described in U.S. Pat. Nos. 7,303,549, 7,137,964, or 6,740,059, each of which is incorporated herein by reference in its entirety.

Drug delivery device 102 typically includes a positive displacement pump mechanism. Typically, the pump mechanism comprises a reservoir that stores the liquid drug. The liquid drug stored in the reservoir may be delivered to the user by expelling the drug from a reservoir using a driven plunger that longitudinally translates though the reservoir to force the liquid drug through a fluid port defined in the reservoir. The plunger may be longitudinally translated through the reservoir by, for example, a rigid leadscrew which pushes the plunger forward during pumping. When the reservoir is filled, the leadscrew travels backwards with the plunger. The leadscrew extends past the back of the plunger a distance equal to the stroke of the plunger plus an additional amount to allow for engagement with the drive mechanism. This leads to a space efficiency constraint when scaling the design. If the stroke of the plunger increases, the length of the leadscrew must increase by the same amount.

In wearable, on-body devices, it is desirable to keep the pump mechanism, as well as the overall drug delivery device 102, as small as possible to minimize the impact to the wearer. Additionally, because such drug delivery devices are typically powered by an on-board battery, it is desirable to minimize the power required to operate the device.

Therefore, it would be desirable to replace the prior art pump mechanism with a positive displacement pump having a more space-efficient pumping mechanism to allow for a smaller device, which would decrease the burden on the user.

Definitions

As used herein, the term "liquid drug" should be interpreted to include any drug in liquid form capable of being administered by a drug delivery device via a subcutaneous cannula, including, for example, insulin, GLP-1, pramlintide, morphine, blood pressure medicines, chemotherapy drugs, fertility drugs or the like or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

A first embodiment of the invention disclosed herein uses a flexible wire to pull the plunger through the reservoir to deliver the liquid drug to the user. A pair of mated rollers grips on the wire and one of the rollers is driven to rotate the rollers, thereby advancing the wire. The wire is fixed to the plunger so that the plunger advances through the reservoir as the wire is pulled by the rollers.

A second embodiment of the invention disclosed herein uses a flexible ribbon instead of a wire to pull the plunger through the reservoir. The ribbon is pulled by a clutch mechanism which grabs the ribbon. The clutch mechanism is coupled to a leadscrew which longitudinally translates the clutch mechanism along the exterior of the reservoir to pull the ribbon, which is coupled to the plunger. The clutch mechanism may be disengaged from the ribbon to allow filling of the reservoir, which requires that the plunger be able to move in a direction opposite the direction in which the ribbon pulls the plunger.

In either embodiment, by having the wire or ribbon configured in as a taut, closed loop, the plunger is supported in both directions, which prevents advancement of the plunger in either direction due to changes in atmospheric pressure. This mechanism also eliminates some challenges that are inherent in a system in which the wire or ribbon is spooled, as spooling changes the distance from the center of the roller to the wire or ribbon, which introduces inaccuracies in the delivery of the liquid drug. The workings of both embodiments is described in further detail below.

BRIEF DESCRIPTION OF THE DRAWINGS

In the drawings, like reference characters generally refer to the same parts throughout the different views. In the following description, various embodiments of the present invention are described with reference to the following drawings, in which:

FIG. 4 is a perspective view of the first embodiment of the invention.

FIG. 6 is a perspective view of the second embodiment of the invention, in which a ribbon is used to pull the plunger through the reservoir.

DETAILED DESCRIPTION

This disclosure presents various systems, components and methods for moving a liquid drug from a liquid reservoir in a drug delivery device to a patient interface, such as a needle or cannula. The embodiments described herein provide one or more advantages over conventional, prior art systems, components and methods, namely, a smaller overall foot-print of the drug delivery device.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
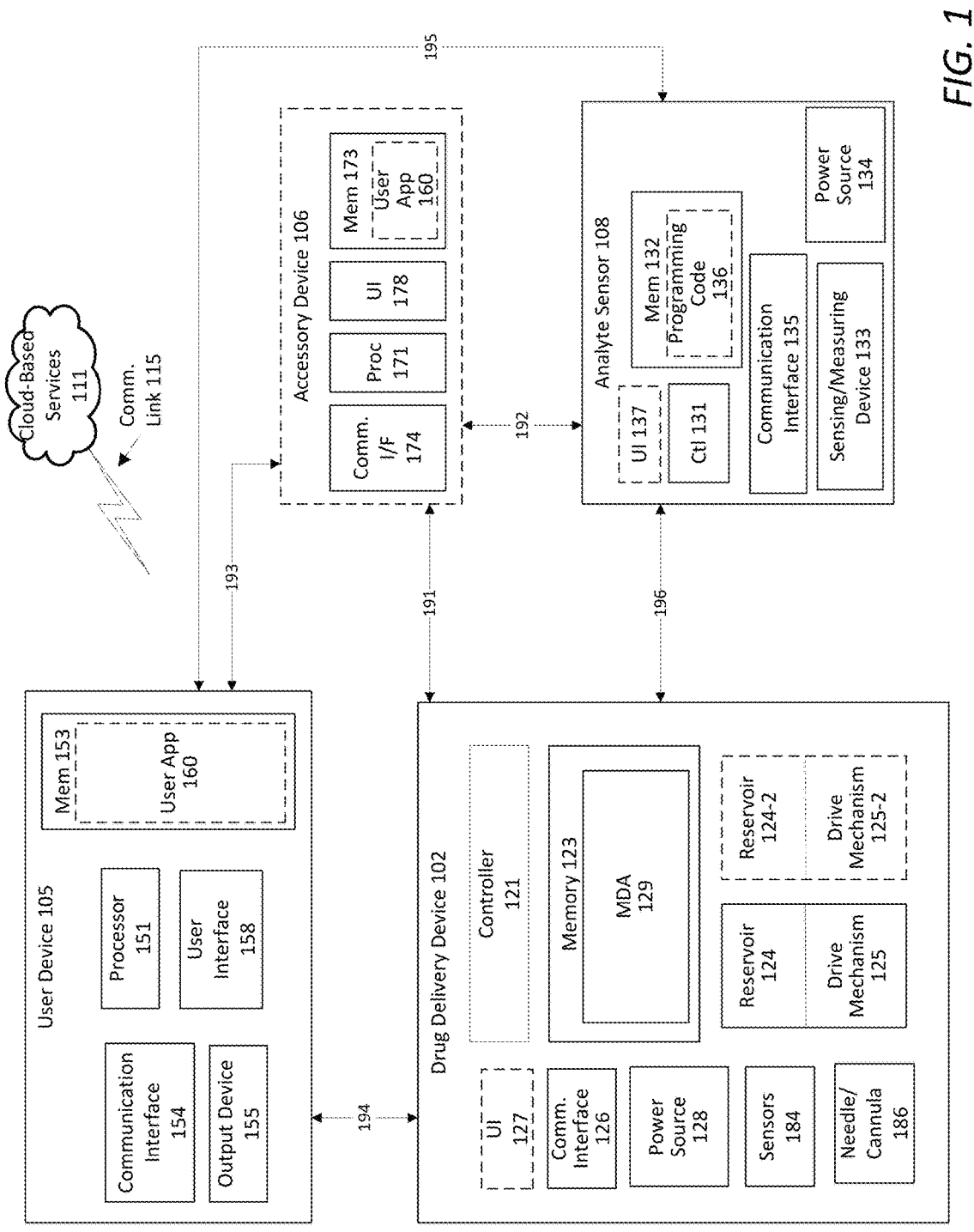
FIG. 1 illustrates a functional block diagram of an exemplary system suitable for implementing the systems and methods disclosed herein.
Figure 2:
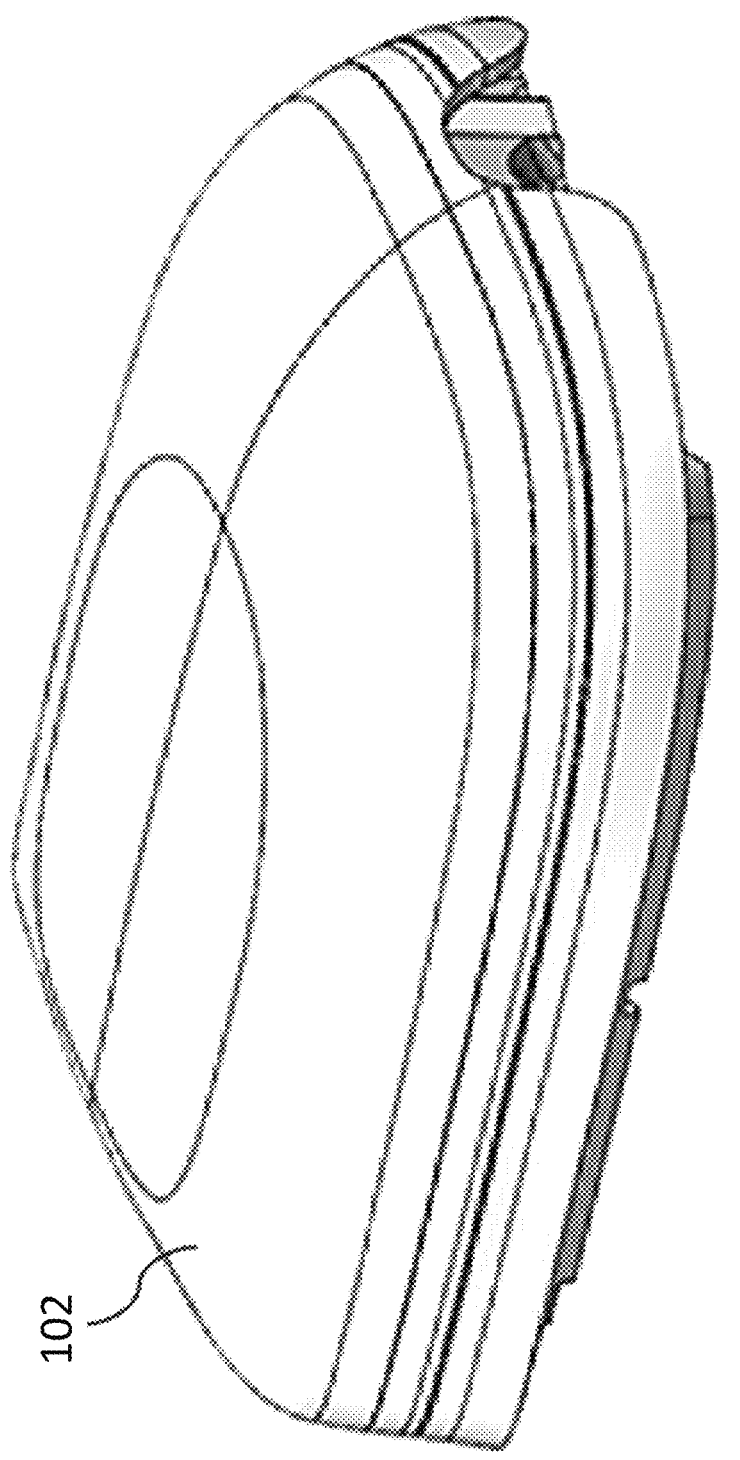
FIG. 2 is a depiction of a prior art wearable drug delivery device of the type in which the invention disclosed herein would be used.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123. Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface may be, for example, a needle or cannula for delivering the drug into the body of the user (which may be done subcutaneously, intraperitoneally, or intravenously). Drug delivery device 102 further includes a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (JOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user, such as a patient or diabetic, at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from respective external devices as well as implementing delivery of a drug to the user according to a diabetes treatment plan or other drug delivery regimen.

Accessory Device

Optional accessory device 107 may be, a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or an attachable housing thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zig-bee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

User app 160 may configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

DESCRIPTION OF EMBODIMENTS

The invention provides two possible embodiments for drive mechanism 125, which is responsible for the longitudinal translation of the plunger through reservoir 124. In general terms, a flexible member is coupled to the plunger and extends through a wall of the reservoir toward which the plunger is being linearly translated. A pulling force on the flexible member causes the plunger to linearly translate toward the end wall of the reservoir, thereby forcing any fluid contained in the reservoir out of the reservoir through a fluid port.

Figure 3:
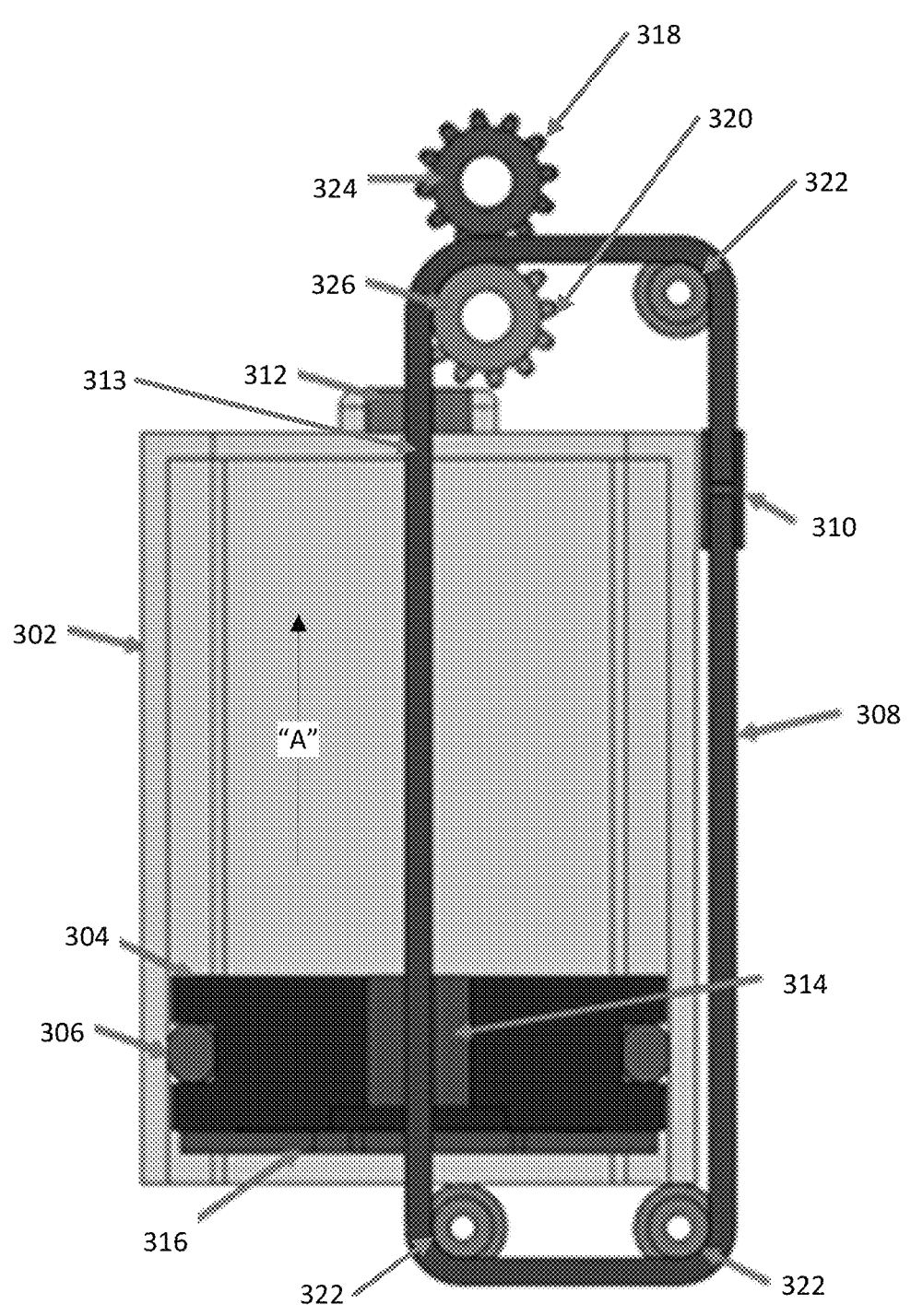
FIG. 3 is a cross-sectional view of a first embodiment of the invention, in which a wire is used to pull the plunger through the reservoir.
Figure 4:
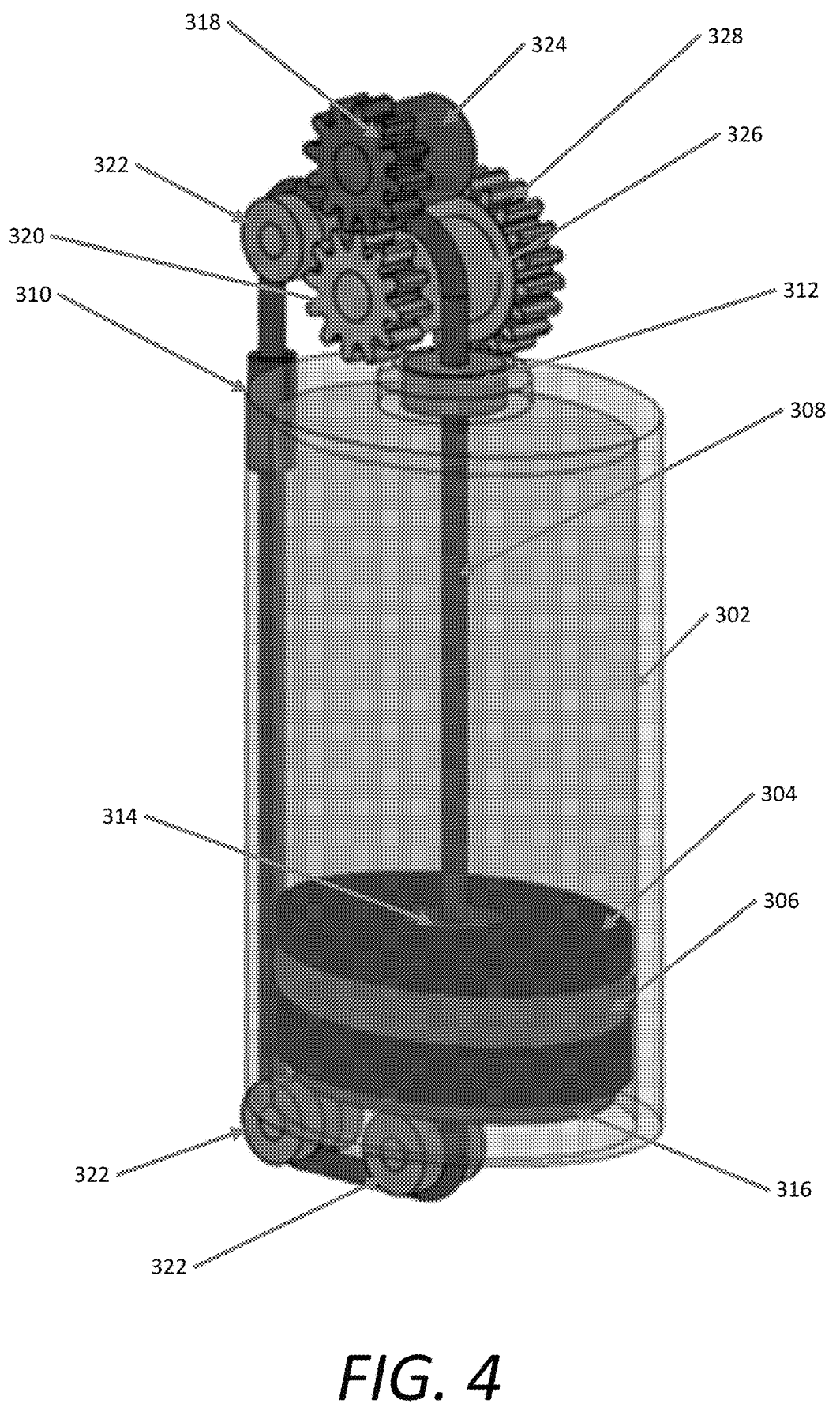

In a first embodiment of the invention is shown in cross-sectional view in FIG. 3 and in perspective view in FIG. 4. A fluid, for example, a liquid drug, is contained within reservoir 302. The reservoir 302 may, in various embodiments of the invention, be composed of polyethylene or an injection-molded plastic, but, in other embodiments, may be composed of any material impermeable to the fluid disposed therein.

The purpose of drive mechanism 125 is to move plunger 304 in direction "A" toward the distal end of reservoir 302, thereby forcing the fluid through an outlet fluid port (not shown) preferably defined in the distal end of reservoir 302. Plunger 304 forms a fluid seal between plunger 304 and the inner wall of reservoir 302 by virtue of O-ring 306, which may be composed of any flexible, fluid-impermeable material, for example, rubber.

In this embodiment, the flexible member is a wire 308 which is rigidly attached to plunger 304 via clip 316 such that movement of wire 308 in direction "A" causes plunger 304 to linearly translate within the interior of reservoir 302 in direction "A" toward the distal end of reservoir 302. Wire 308 passes through plunger 304 and septum 314, which forms a fluid seal between wire 308 and plunger 304. In addition, wire 308 also passes through opening 313 in reservoir 302 which is sealed by septum 312.

In preferred embodiments of the invention, wire 308 may be a stranded wire allowing for higher strength-to-flexibility ratio, however, in other embodiments of the invention, a solid wire may be used. In some embodiments, wire 308 is composed of strands of stainless steel or copper, but other materials may also be used. Preferably, wire 308 is covered by a layer of insulation such as to be able to maintain a fluid-tight seal with septum 314 and septum 312. In some embodiments, the insulation may be Polytetrafluoroethylene (PTFE), but any other suitable material may also be used.

Wire 308 is pulled in direction "A" by action of rollers 324 and 326. The insulation on wire 308 aids in the frictional engagement between wire 308 and rollers 324, 326, which may, in some embodiments, have knurling defined on the surface thereof to aid in the gripping of wire 308. Rollers 324, 326 are mated together with spur gears 318, 320, coupled rollers 324, 326 respectively, to ensure that rollers 324, 326 move in unison to prevent slippage of wire 308. In preferred embodiments of the invention, one or the other of rollers 324, 326 is driven by a motor. As shown in FIG. 4, gear 320 is coupled to gear 328 by roller 326. Gear 328 is coupled to a motor (not shown) directly or via one or more other gears (not shown) such that rotation of the motor will cause a rotational movement of both gears 318 and 320 and, in turn, rollers 324, 326. In other embodiments of the invention, gear 318 may be the driven gear.

The ends of wire 308 are coupled by wire crimp 310, such that the wire forms a continuous, taut loop, supported by dummy rollers 322, and extending through plunger 304 and the interior of reservoir 302. The taut loop prevents unwanted movement of plunger 304 in either direction due to, for example, changes in atmospheric pressure or other forces.

In certain embodiments of the invention, a clutch mechanism (not shown) may be provided which will disengage rollers 324, 326 from wire 308 to allow plunger 304 to move in a direction opposite direction "A", to allow filling of the reservoir. In other embodiments, gears 318, 320, may be driven such as to cause wire 308 to move plunger 304 in a direction opposite direction "A".

Figure 5:
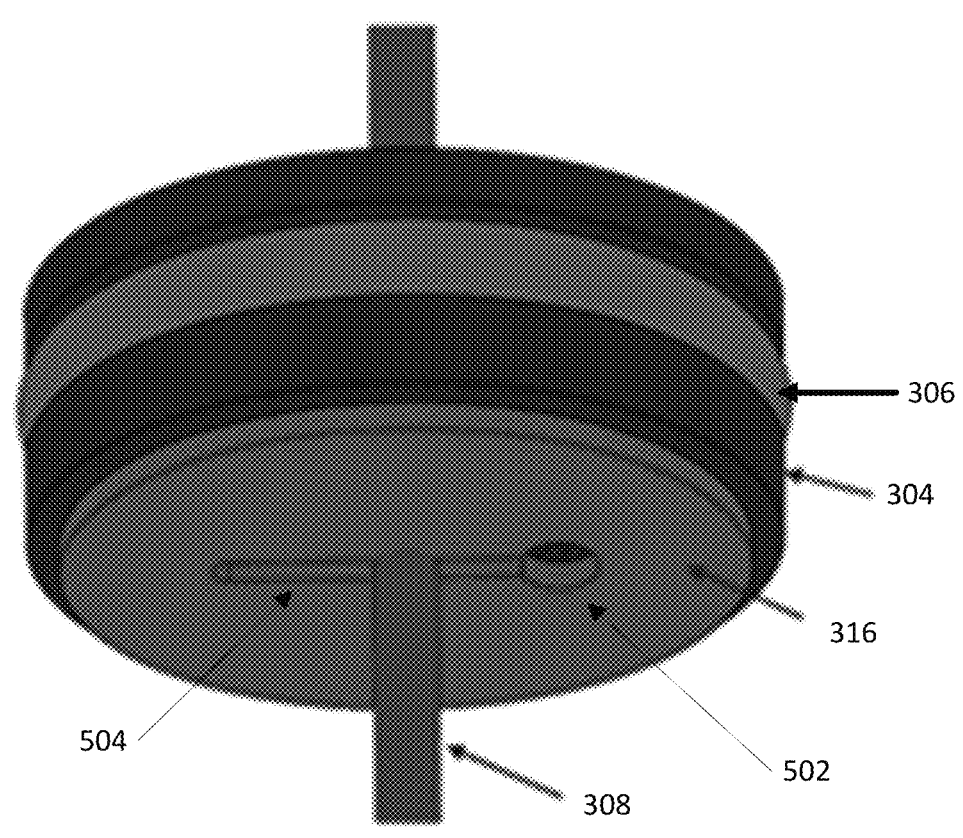
FIG. 5 is a drawing showing one possible embodiment of a wire clip for use with the first embodiment for attaching the wire to the plunger.

One possible embodiment of wire clip 316 is shown in FIG. 5. In this embodiment, wire 308 is passed through opening 502 prior to wire 308 being formed into a loop by engagement with wire crimp 310. Wire 308 is then slid into slot 504 such at the edges of slot 504 engage the insulation of wire 308, thereby causing a coupling between wire clip 316 and wire 308. Wire clip 316 may be permanently attached to plunger 304, by, for example, an adhesive or other means. In other embodiments, wire clip 316 may not be permanently attached to plunger 304 but is nevertheless able to move plunger 30 or by virtue of a force applied by the movement of wire 308 in direction "A". As would be realized by one of skill in the art, wire clip 316 shown in FIG. 5 is only one possible embodiment of a means for attaching wire 308 to plunger 304. In other embodiments of the invention, any other means may be used to attach wire 308 to plunger 304.

Figure 6:
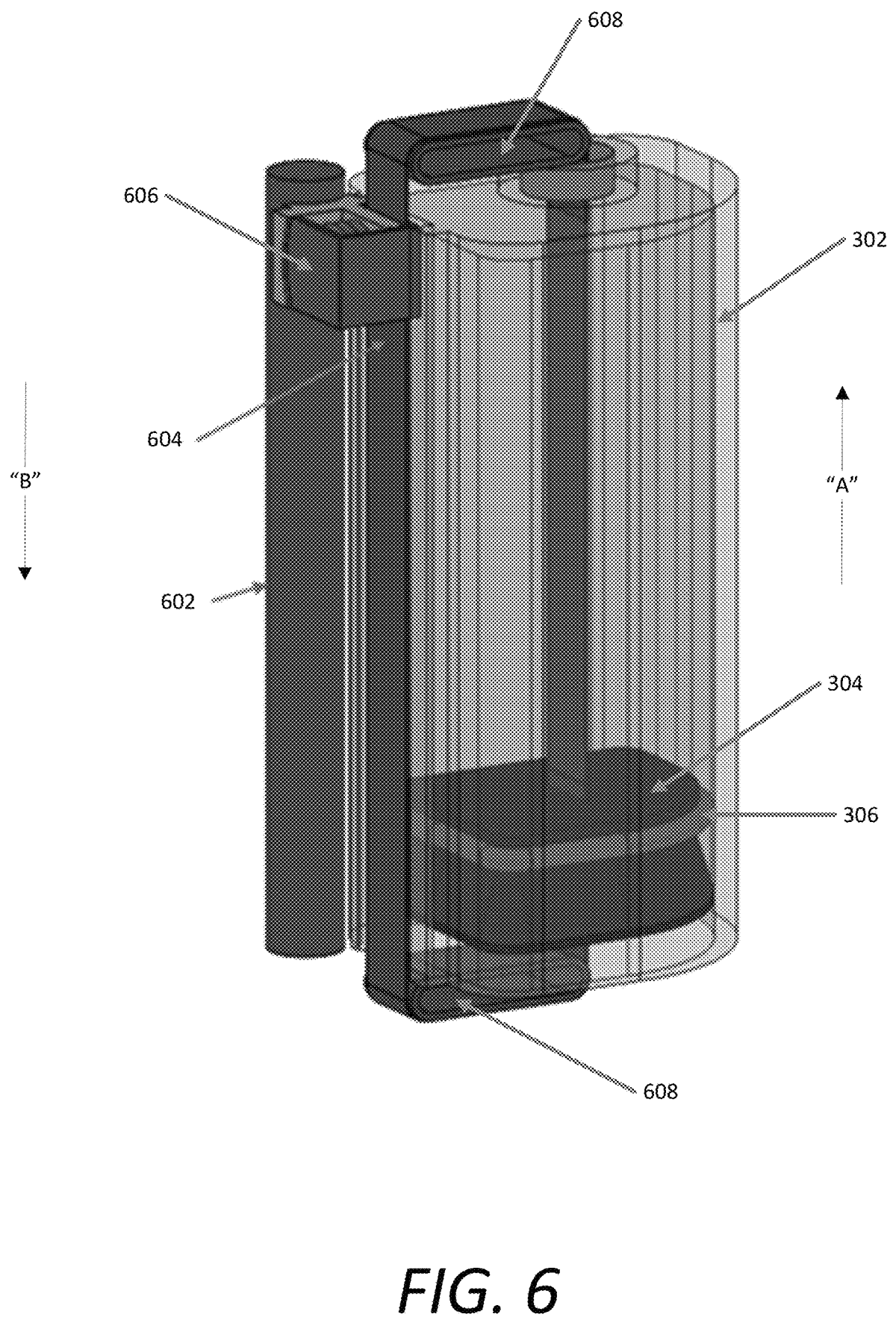

A second embodiment of the invention is shown in perspective view in FIG. 6. In this embodiment, the flexible member comprises ribbon 604, which is rigidly attached to plunger 304 by any known means. In preferred embodiments of the invention, the ribbon 604 may be composed of a coated fiberglass or metal. In other embodiments of the invention, any other suitable material may be used.

Figure 7:
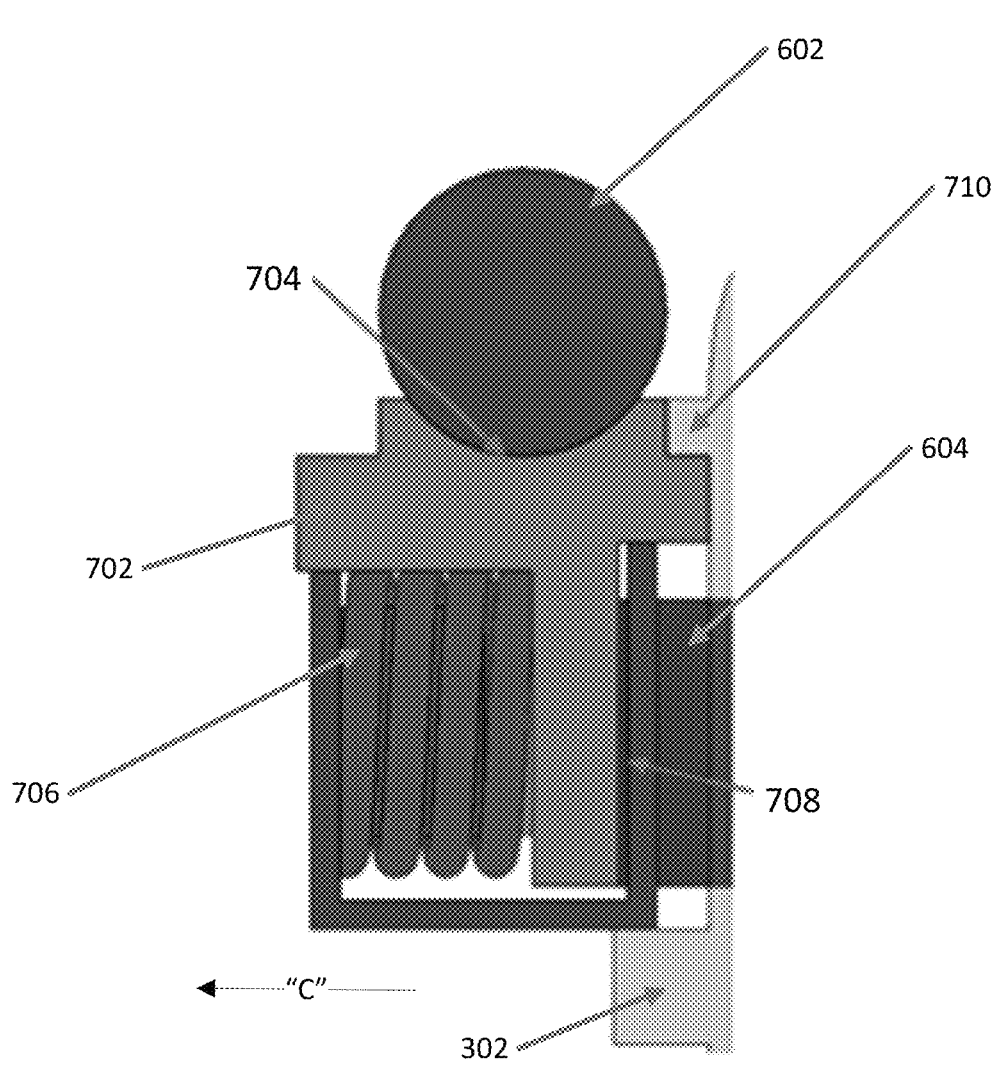
FIG. 7 is a top view of the clutch mechanism used with the second embodiment of the invention.

Ribbon 604 is driven by clutch mechanism 606 which is caused to move in direction "B" by virtue of a threaded engagement 704 with leadscrew 602, as shown in a top view in FIG. 7. Rotation of lead screw 602 causes movement of clutch 606 in direction "B" which, in turn, causes the linear translation of plunger 304 through the interior of reservoir 302 in direction "A". Leadscrew 602 may be rotationally driven by a motor (not shown) which may be coupled to leadscrew 602 via one or more gears (not shown).

Ribbon 604 is formed into a taut loop and held in place by guides 608 located at the top and bottom of reservoir 302. Preferably guides 608 are composed of a low-friction material or may be lubricated to allow the unimpeded movement of ribbon 604 over guides 608. In alternate embodiments of the invention, dummy rollers of the type shown in FIG. 3 as reference number 322 may also be used.

Clutch mechanism 606 is shown in top view in FIG. 7. Clutch mechanism 606 comprises a housing 702 which is in threaded engagement 704 with leadscrew 602. Spring 706 causes movement of engagement member 708 in direction "C", which causes a frictional engagement of ribbon 604 between engagement member 708 and housing 702, such that the movement of clutch 606 in direction "B" also causes movement of ribbon 604. Clutch 606 may initially be disengaged from ribbon 604 by, for example, a trigger mechanism (not shown) which holds engagement member 708 such as to not be frictionally engaged with ribbon 604. This allows the free movement of ribbon 604 in either direction so as to allow movement of plunger 304 in direction "B" to allow filling of reservoir 302 with the liquid drug. Once reservoir 302 is full, the trigger mechanism may be tripped, causing engagement member 708 to move in direction "C" by virtue of the action of spring 706, and into frictional engagement with ribbon 604. The exterior surface of reservoir 302 may define a guide 710 which engages housing 702 of clutch 606 to guide the movement of clutch 606 along the exterior of reservoir 302.

The following examples pertain to various embodiments of the systems and methods disclosed herein for implementation of an automatic drug delivery system dispensing with Pramlintide and insulin.

Example 1 is a first embodiment of a device comprising a reservoir, a plunger configured to be linearly translated through the reservoir, a flexible member rigidly coupled to the plunger and a drive mechanism for pulling the flexible member to cause the linear translation of the plunger through the reservoir.

Example 2 is an extension of Example 1, or any other example disclosed herein, wherein the device further comprises a fluid port, defined in the reservoir such that a linear translation of the plunger through the reservoir forces a fluid contained in the reservoir through the fluid port.

Example 3 is an extension of Example 1, or any other example disclosed herein, wherein the flexible member is a wire.

Example 4 is an extension of Example 3, or any other example disclosed herein, wherein the device further comprises an opening defined in end of the reservoir and a septum sealing the opening along the wire it passed therethrough.

Example 5 is an extension of Example 1, or any other example disclosed herein, wherein the drive mechanism comprises a pair of rollers in frictional engagement with the wire and rotating in opposite directions.

Example 6 is an extension of Example 5, or any other example disclosed herein, wherein the drive mechanism further comprises a gear coupled to each of the rollers, wherein the gears are in rotational engagement with each other.

Example 7, is an extension of Example 6, or any other example disclosed herein, wherein at least one of the gears is rotationally driven such as to cause a rotation of the rollers in opposite directions.

Example 8 is an extension of Example 3, wherein the wire is insulated such as to be able to form a fluid seal with the septum.

Example 9 is an extension of Example 8, or any other example disclosed herein, wherein a circumferential surface of each of the rollers defines the knurled pattern such as to cause a frictional engagement with the insulation of the wire.

Example 10 is an extension of Example 3, or any other example disclosed herein, wherein the wire is a stranded wire.

Example 11 is an extension of Example 3, or any other example disclosed herein, wherein the wire forms a complete, taut loop and further wherein the wire passes through the plunger such as to prevent movement of the plunger absent a movement of the wire caused by the drive mechanism.

Example 12 is an extension of Example 11, or any other example disclosed herein, wherein the device further comprises a plurality of roller members performing the wire into the taut loop.

Example 13 is extension of Example 1, or any other example disclosed herein, wherein the flexible member is a ribbon.

Example 14 is an extension of Example 11, or any other example disclosed herein, wherein rotation of the leadscrew causes a linear translation of the clutch mechanism along an outside surface of the reservoir.

Example 15 is an extension of Example 14, or any other example disclosed herein, wherein the clutch mechanism comprises a housing, a spring in an engagement member, wherein the spring holds ribbon and frictional engagement between the housing in the engagement member.

Example 16 is extension of Example 15, or any other example disclosed herein, wherein the clutch mechanism further comprises a trigger mechanism for holding the engagement member away from the ribbon such as to allow free movement of the ribbon prior to the trigger mechanism being tripped.

Example 17 is an extension of Example 14, or any other example disclosed herein, wherein an exterior surface of the reservoir defines a guide thereon for guiding the clutch mechanism along the exterior surface of the reservoir.

Example 18 is an extension of Example 13, or any other example disclosed herein, wherein the ribbon is composed of coated fiberglass or metal.

Example 19 is an extension of example 13, or any other example disclosed herein, wherein the ribbon forms a complete, taut loop and further wherein the ribbon passes through the plunger such as to prevent movement of the plunger absent a movement of the ribbon caused by the drive mechanism.

Example 20 is an extension of Example 19, or any other example disclosed herein, wherein the device further comprises a plurality of rollers performing the ribbon into the taut loop.

Example 21 is a method of linearly translating the plunger to a reservoir comprising attaching a flexible member to the plunger, the flexible member passing through a wall of the reservoir toward which the plunger is being linearly translated and pulling the flexible member to linearly translate the plunger toward the wall of the reservoir.

Example 22 is an extension of example 21, or any other example defined herein, wherein the flexible member is an insulated wire or ribbon.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the invention relates, many modifications and adaptations of the invention may be realized. Implementations provided herein, including sizes, shapes, ratings and specifications of various components or arrangements of components, and descriptions of specific manufacturing processes, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A device comprising:
a reservoir having walls including a first wall and a second wall and a distal end comprising a fluid port;
a plunger configured to be linearly translated through the reservoir;
a flexible member, rigidly coupled to the plunger, that is configured to move across an interior of the reservoir inside the walls in a longitudinal direction towards the distal end of the reservoir, and configured to move across an exterior of the reservoir outside the walls in a reverse-longitudinal direction opposite the longitudinal direction, wherein the flexible member extends through the first wall at the distal end of the reservoir and through the second wall of the reservoir on a second end opposite the distal end; and
a drive mechanism for pulling the flexible member to cause a linear translation of the plunger through the reservoir.

2. The device of claim 1,
wherein linear translation of the plunger through the reservoir forces a fluid contained in the reservoir through the fluid port.

3. The device of claim 1, wherein the flexible member is a wire.

4. The device of claim 3, further comprising:
an opening, defined in an end of the reservoir; and
a septum, sealing the opening and allowing the wire to pass therethrough.

5. The device of claim 3, wherein the drive mechanism comprises:
a pair of rollers in frictional engagement with the wire and rotating in opposite directions.

6. The device of claim 5, further comprising:
a gear, coupled to each of the rollers;
wherein the gears are in rotational engagement with each other.

7. The device of claim 6 wherein at least one of the gears is rotationally driven such as to cause the rotation of the rollers in opposite directions.

8. The device of claim 3 wherein the wire is insulated such as to be able to form a fluid seal with a septum.

9. The device of claim 8 wherein a circumferential surface of each of a pair of rollers defines a knurled pattern, such as to cause a frictional engagement with the insulation of the wire.

10. The device of claim 3 wherein the wire is a stranded wire.

11. The device of claim 3 wherein the wire forms a complete, taut loop and further wherein the wire passes through the plunger such as to prevent movement of the plunger absent a movement of the wire caused by the drive mechanism.

12. The device of claim 11 further comprising:
a plurality of roller members for forming the wire into the taut loop.

13. The device of claim 1, wherein the flexible member is a ribbon.

14. The device of claim 13 wherein the drive mechanism comprises:
a clutch mechanism engaging the ribbon; and
a leadscrew in threaded engagement with the clutch mechanism, wherein rotation of the leadscrew causes a linear translation of the clutch mechanism along an outside surface of the reservoir.

15. The device of claim 14, wherein the clutch mechanism comprises:
a housing;
a spring; and
an engagement member;
wherein the spring holds the ribbon in frictional engagement between the housing and the engagement member.

16. The device of claim 15 wherein the clutch mechanism further comprises:
a trigger mechanism for holding the engagement member away from the ribbon such as to allow free movement of the ribbon prior to the trigger mechanism being tripped.

17. The device of claim 14 wherein an exterior surface of the reservoir defines a guide thereon and further wherein the clutch mechanism is engaged with the guide as the clutch mechanism translates linearly along the exterior surface of the reservoir.

18. The device of claim 13 wherein the ribbon is composed of coated fiberglass or metal.

19. The device of claim 13 wherein the ribbon forms a complete, taut loop and further wherein the ribbon passes through the plunger such as to prevent movement of the plunger absent a movement of the ribbon caused by the drive mechanism.

20. The device of claim 19 further comprising:
a plurality of rollers for forming the ribbon into the taut loop.

21. The device of claim 1, wherein the flexible member is configured to move in the longitudinal direction inside the reservoir at a same time as the flexible member is configured to move in the reverse longitudinal direction outside the reservoir.

22. A method of linearly translating a plunger through a reservoir, the reservoir comprising walls including a first wall and a second wall and a distal end comprising a fluid port, the method comprising:
attaching a flexible member to the plunger, the flexible member passing through the first wall of the reservoir toward which the plunger is being linearly translated and the second wall on an opposite side of the reservoir from the first wall; and
pulling the flexible member to linearly translate the plunger across an interior of the reservoir inside the walls of the reservoir in a longitudinal direction toward the distal end of the reservoir, and across an exterior of the reservoir outside the walls of the reservoir in a reverse-longitudinal direction opposite the longitudinal direction.

23. The method of claim 22 wherein the flexible member is an insulated wire or a ribbon.

* * * * *